United States Patent [19]
Bossler et al.

[11] Patent Number: 5,344,528
[45] Date of Patent: Sep. 6, 1994

[54] RECOVERY OF PHENOL FROM LOW CONCENTRATIONS WITH SODIUM SULFATE

[75] Inventors: Thomas H. Bossler, Washington Township, Westmoreland County; Donald Glassman, Mt. Lebanon Township, Allegheny County; Michael C. Grebinoski, West Deer Township, Allegheny County; Howard H. Morgan, Jr., Monroeville Boro, Allegheny County; Jennifer L. Voss, Bethel Park, all of Pa.

[73] Assignee: Aristech Chemical Corporation, Pittsburgh, Pa.

[21] Appl. No.: 102,185

[22] Filed: Aug. 4, 1993

[51] Int. Cl.$^5$ .......................... B01D 3/34; C07C 37/74
[52] U.S. Cl. ............................. 203/14; 203/18; 203/27; 203/33; 203/47; 203/48; 203/50; 203/98; 203/DIG. 25; 568/749; 568/759
[58] Field of Search ............... 203/33, 14, 18, 50, 203/48, 47, 27, DIG. 25, 98; 568/749, 759, 754, 755

[56] References Cited

U.S. PATENT DOCUMENTS

| | | | |
|---|---|---|---|
| 1,931,057 | 10/1933 | Clemmensen et al. | 203/33 |
| 2,084,419 | 6/1937 | Wallis et al. | 203/33 |
| 2,573,244 | 10/1951 | Bogart et al. | 202/68 |
| 2,597,497 | 5/1952 | Joris | 260/593 |
| 3,075,015 | 1/1963 | Meyer et al. | 260/586 |
| 3,829,509 | 8/1974 | Charles et al. | 568/749 |
| 3,846,255 | 11/1974 | Sisk | 568/749 |
| 4,016,049 | 4/1977 | Fozzard et al. | 203/60 |

Primary Examiner—Wilbur Bascomb, Jr.
Attorney, Agent, or Firm—William L. Krayer

[57] ABSTRACT

Phenol plant waste water containing small amounts of phenol and sodium sulfate is successfully distilled through the addition of recovered sodium sulfate to enhance the volatility of the phenol relative to water; at least a portion of the sodium sulfate is recycled, while a significant portion of the phenol can be returned to the phenol plant for recovery.

7 Claims, 1 Drawing Sheet

RECOVERY OF PHENOL FROM LOW CONCENTRATIONS WITH SODIUM SULFATE

TECHNICAL FIELD

This invention relates to the recovery of phenol from water containing about 0.5 to about 4 percent phenol and about 5% to about 18% sodium sulfate. This invention also relates to the preparation of phenol plant waste water for introduction to a biological or other waste treatment plant, by reducing the concentration of phenol therein. It also relates to the use of relatively high concentrations of sodium sulfate in a water/phenol azeotrope to enhance the relative volatility of the phenol during distillation of the azeotrope, thereby enhancing the recovery of phenol. And it relates to an energy-efficient combination of the use of concentrations of sodium sulfate higher than 8% to improve the volatility of phenol by recycling sodium sulfate from a phenol plant waste water stream.

BACKGROUND OF THE INVENTION

It is well known that phenol and water form an azeotrope which is difficult to separate. Where it is desired also to remove substantial amounts of inorganic salts from mixtures of phenol and water, the process parameters become perhaps even more complicated.

In Volume 44, No. 2 of Chemical Engineering Progress (1948), Bogart and Brunjes reported, in "Distillation of Phenolic Brines", experiments on separations of a phenol-water-salt mixture of a type obtained from the neutralization of sodium phenate with hydrochloric acid. They observed that sodium chloride in relatively high concentrations performed a function similar to that of a selective solvent in extractive distillation, making feasible (although still difficult) the recovery of phenol from relatively weak solutions. According to Bogart and Brunjes, the typical phenol-water-salt mixture from the neutralization of sodium phenate will contain about 6.7% phenol. Furthermore, in the process they employed to enhance the separation of phenol, the azeotrope composition containing 9.2 weight percent phenol was found to provide the "maximum enrichment".

In U.S. Pat. 3,829,509, Charles et al disclose the addition of calcium or magnesium chloride to an aqueous solution of phenol and hydrogen chloride to enhance the separation of the phenol and the hydrogen chloride by distillation. The high concentrations of calcium or magnesium chloride apparently increase the relative volatility of the hydrogen chloride and the phenol. The system is different from that of the inventors herein, in that the present system treats a waste water system from a phenol plant, which includes substantial amounts of sodium sulfate.

SUMMARY OF THE INVENTION

This invention was developed to deal with a waste stream from a phenol plant, comprising about 0.5 to about 4% phenol, about 8 to about 18% sodium sulfate, and the balance water with up to as much as about 1% other organics. The objective was to remove as much of the sodium sulfate and the phenol as possible before sending the stream to a biological waste treatment plant.

The invention includes a method of removing phenol from an aqueous medium where it resides in concentrations from about 0.5% to about 4% by distilling the aqueous medium containing the phenol in the presence of about 8% to about 18% by weight sodium sulfate, at least 20% of which may be introduced from a sodium sulfate recovery system for the waste water. The condensate from the distillation step is cooled and separated into a phenol-rich layer and a water-rich layer. The phenol-rich layer contains at least 60% phenol and may be returned to the phenol plant or otherwise used for its high phenol content. The water-rich layer is preferably refluxed back to the distillation step.

It is desired to substantially remove both the phenol and the sodium sulfate before forwarding the stream to a biological or other waste treatment facility. Prior to distillation, the feed stream may be mixed with a second phenol-containing stream, which is a water-rich portion of condensate from the distillation step, thus increasing the phenol content to a concentration of up to about 8% and sodium sulfate is added to the mixed stream to maintain its concentration at about 8% to about 12% by weight. This mixed stream containing 10% more or less sodium sulfate is fed to the top of a distillation tower. As related previously, condensate from the distillation step is separated into a water-rich layer and a phenol-rich layer; the bottoms, containing about 15% to about 25% sodium sulfate, are sent to an evaporative crystallizer. Heat removed in the condensation step is used in the evaporative crystallizer. The crystallization step is preferably conducted at a pH of about 3 to about 6. The sodium sulfate crystals obtained in the crystallizer are relatively pure and can find commercial uses; however, a portion of them are recycled to increase the sodium sulfate concentration of the material fed to the distillation tower. The water-rich layer is recycled to the distillation tower, and the phenol-rich layer can be recycled to the phenol plant. Thus, substantial portions of both the phenol and the sodium sulfate in the waste water are recovered for commercial uses.

DETAILED DESCRIPTION OF THE INVENTION

Figure 1:
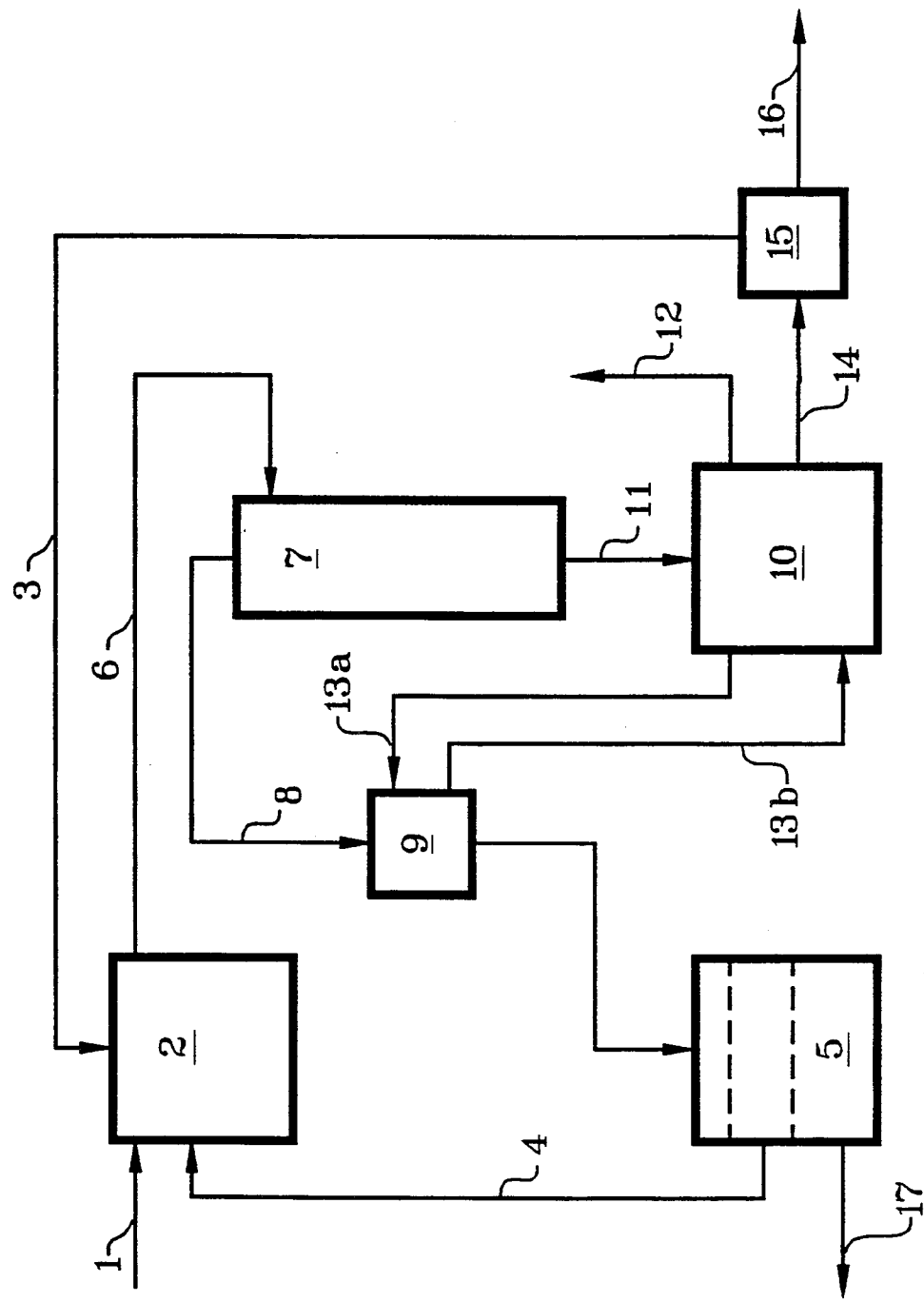

Our system for the treatment of waste streams to remove substantial amounts of sodium sulfate and moderate amounts, i.e. about 0.5 to about 4%, of phenol will be described with reference to the accompanying drawing, wherein FIG. 1 represents a block diagram or flow sheet of the preferred process.

A typical process will be described with reference to FIG. 1. Feed line 1 preferably has been treated to remove trace amounts of heavies and to reduce the pH to around 5. The typical feed contains, by weight, 84.5% water, 14.2% sodium sulfate, and 1.4% phenol. It is passed to mixing tank 2 where it is mixed with two recycle streams—one in line 3 containing concentrated sodium sulfate, and one in line 4 containing a water-rich phenol-containing portion from the condensate separator 5. The solution passing from the mixing tank in line 6 contains 84.7% water, 10.5% sodium sulfate, and 4.8% phenol. It is sent to the top of tower 7 for distillation. The tower 7 has 42 trays and operates at a pressure of about 35 psia. The overhead vapor is sent through line 8 to the heat exchanger 9 for the evaporative crystallizer 10, and the condensate is collected and separated in separator 5. The phenol-rich portion of the material in separator 5 is sent back in line 17 to the phenol plant for introduction to a stream of about the same composition, not shown, or for other use of its phenol value. The bottoms from tower 7 are sent through line 11 after acidification to a pH of 4.5 (through an acid addition not shown) to evaporative crystallizer 10. Impurities may be removed from the crystallizer through line 12. Material in the crystallizer is circulated through line 13a through heat exchanger 9 to draw heat from the condensation of the overhead vapor from tower 7, bringing the heat energy back through line 13b to crystallizer 10 to aid in the evaporation process. The solution passing from crystallizer 10 through line 14 is sent to centrifuge 15 where a composition is made comprising 90% sodium sulfate and 10% water. A portion of this is recycled in line 3 to mixing tank 2 and the balance is exported by line 16 for drying and/or other use of its sodium sulfate value, Our invention may be otherwise variously practiced within the scope of the following claims.

We claim:

1. Method of removing phenol values from concentrations of about 0.5 weight percent to about 4 weight percent in an aqueous solution comprising conducting a distillation of said aqueous solution in the presence of about 8 weight percent to about 18 weight percent sodium sulfate, condensing vapor from said distillation, collecting the condensate therefrom in water-rich and phenol-rich portions, and recovering phenol values from said phenol-rich portion.

2. Method of claim 1 wherein a phenol-bearing stream is added to said solution prior to distillation, thereby attaining a phenol concentration of up to about 8%.

3. Method of claim 1 wherein a portion of said sodium sulfate, is recovered from the bottoms of said distillation and recycled to said aqueous solution.

4. Method of claim 3 wherein the sodium sulfate is recovered by concentrating said bottoms.

5. Method of claim 3 wherein the sodium sulfate is recovered by evaporative crystallization from said bottoms at a pH of about 3 to about 6, and wherein heat energy is utilized from the condensation of said vapor.

6. Method of claim 5 followed by centrifugation of said sodium sulfate to recover sodium sulfate crystals.

7. Method of recovering phenol and sodium sulfate from an aqueous waste stream comprising sodium sulfate and about 0.5% to about 4% phenol comprising adding sodium sulfate thereto to attain about 8% to about 18% sodium sulfate, distilling said stream to obtain an overhead fraction and a bottoms stream, recovering a phenol stream and a water-rich phenol-containing stream from the overhead fraction, recovering sodium sulfate from the bottoms, recycling at least a portion of said recovered sodium sulfate to said stream at a point prior to said distillation, and recycling said water-rich phenol-containing stream to said aqueous waste stream.

* * * * *